United States Patent [19]

Kuo

[11] 4,220,717
[45] Sep. 2, 1980

[54] **ISOLATION AND PURIFICATION OF POLYRIBOSYL RIBITOL PHOSPHATE FROM *HAEMOPHILUS INFLUENZAE* TYPE B.**

[75] Inventor: Joseph S.-C. Kuo, Orangeburg, N.Y.

[73] Assignee: American Cyanamid Company, Stamford, Conn.

[21] Appl. No.: 846,488

[22] Filed: Dec. 22, 1977

[51] Int. Cl.$^2$ .............................................. C12D 13/04
[52] U.S. Cl. .................................. 435/101; 435/803; 435/851; 424/92; 536/1
[58] Field of Search ................... 536/1; 195/31 P, 96; 424/92, 88

[56] References Cited

U.S. PATENT DOCUMENTS 3,978,209  8/1976  Limjuco et al. ...................... 424/92

OTHER PUBLICATIONS

Rodriques, et al., "Immunity to *Haemophilus influenzae* type b. I. Isolation, and Some Physiochemical, Serologic and Biologic Properties of the Capsular Polysaccharide of *Haemophilus influenzae* type b.", *Chem. Abst.*, vol. 75, No. 20, p. 107, Abs. No. 116864n, (1971).
Branefors-Helander, et al., "Structural Studies of the Capsular Antigen from *Haemophilus influenza* type b.", *Chem. Abst.*, vol. 84, No. 23, p. 309, Abs. No. 162787y, (1976).
Branefors-Helander, et al., "The Structure of the Capsular Antigen from *Haemophilus influenza* type A.", *Chem. Abst.*, vol. 87, No. 5, p. 345, Abs. No. 37200n, (1977).

*Primary Examiner*—Thomas G. Wiseman
*Attorney, Agent, or Firm*—Thomas M. Saunders

[57] ABSTRACT

A process for the isolation and purification of immunologically active polyribosyl ribitol phosphate (PRP), the capsular polysaccharide of *Haemophilus influenzae* type b. The PRP has been purified with ethanol, Cetavlon (hexadecyltrimethyl ammonium bromide) and a phosphate containing adsorbent, hydroxylapatite. The contaminants (nucleic acid, proteins and endotoxins) are removed to the minimum level by a treatment with hydroxylapatite. Also described is a process for the preparation of a combined vaccine containing the PRP (prepared as aforementioned) and *B. pertussis* antigens. The vaccine elicits anti-PRP antibody and antipertussis antibody (as measured by microagglutination) formations in young animals. This sera with anti-PRP antibody exhibits a strong bactericidal activity.

2 Claims, 3 Drawing Figures

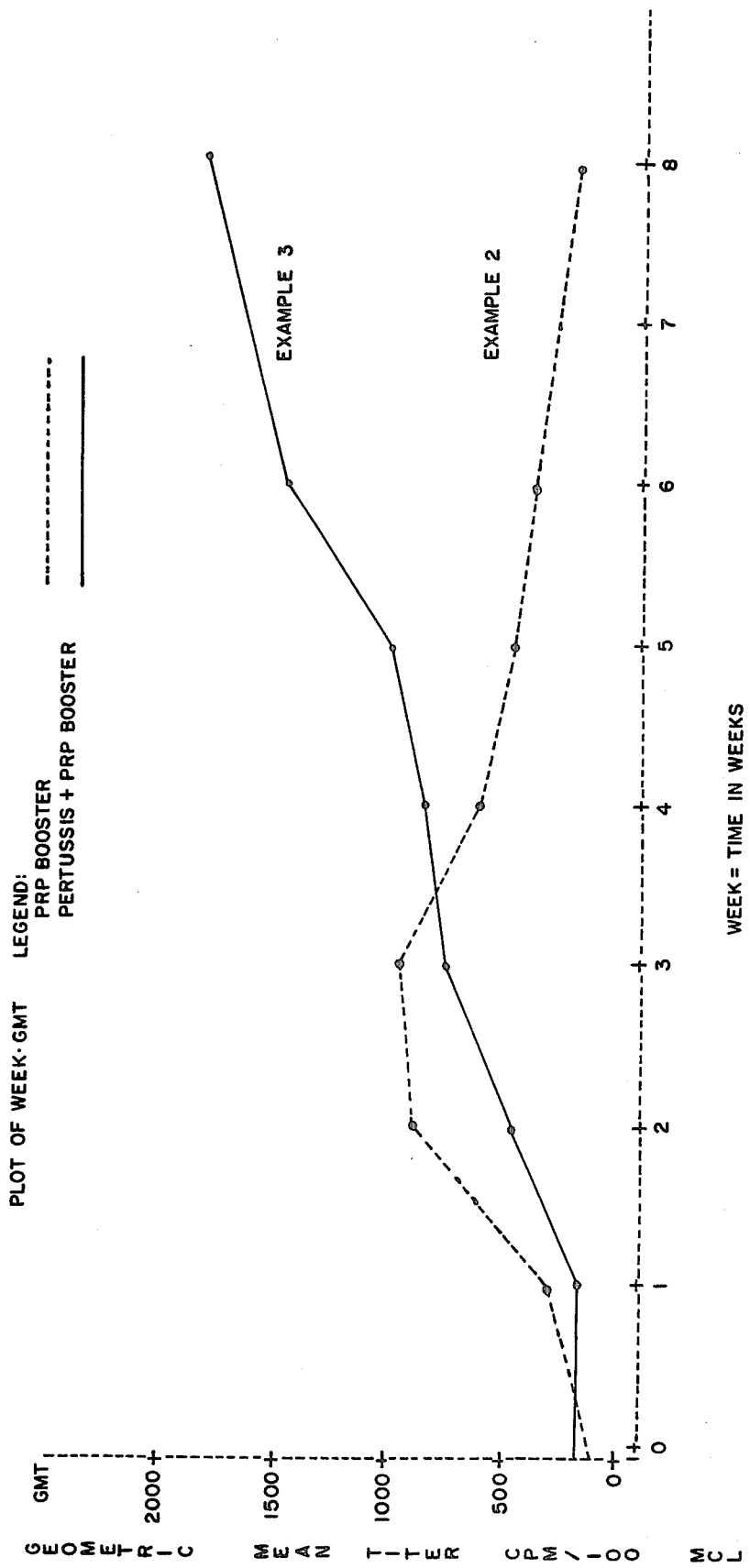

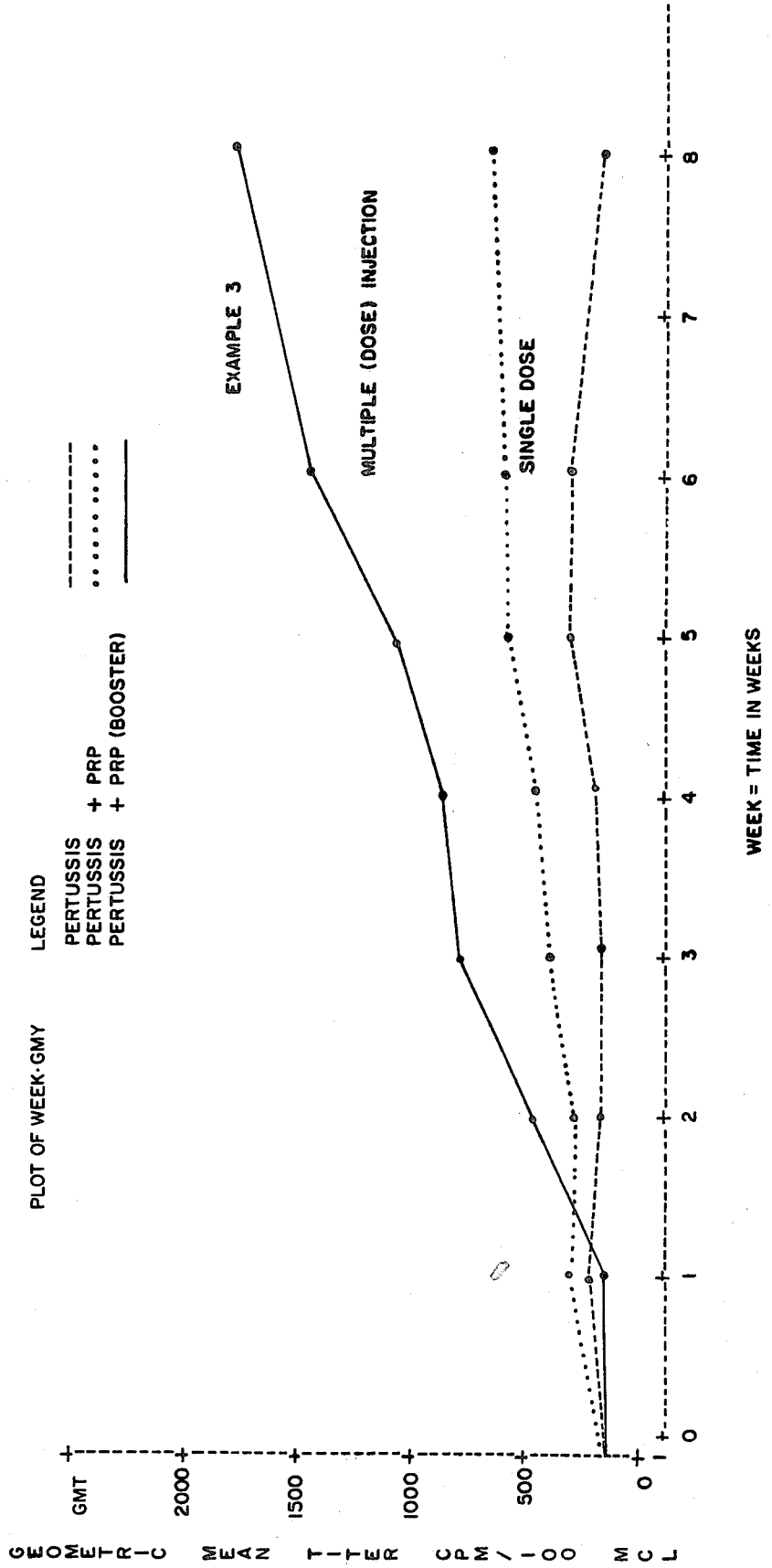

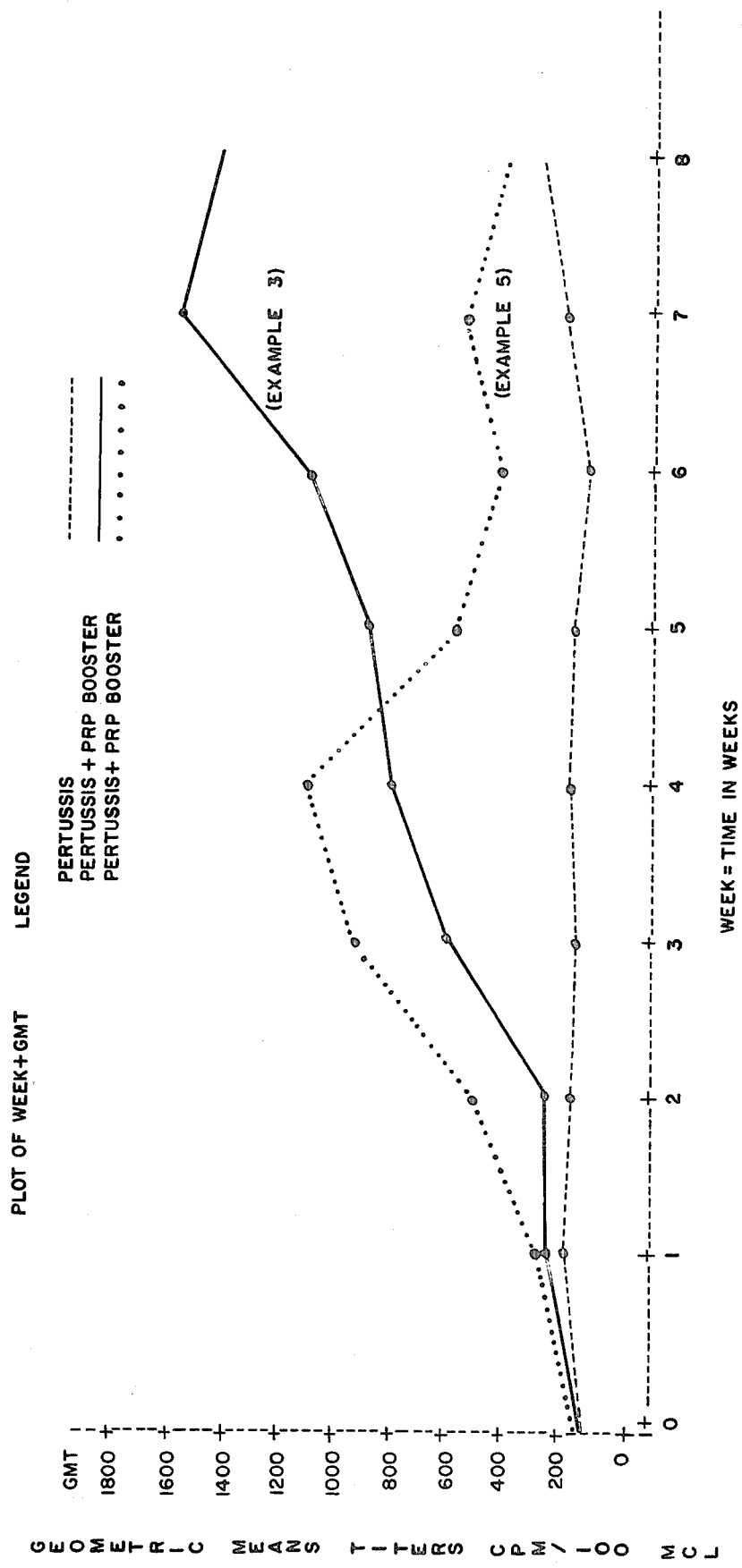

ISOLATION AND PURIFICATION OF POLYRIBOSYL RIBITOL PHOSPHATE FROM *HAEMOPHILUS INFLUENZAE* TYPE B.

BACKGROUND OF THE INVENTION

Applicant is not aware of any prior art references which, in his judgement as one skilled in the art, would anticipate or render obvious the instant invention; however, for the purpose of fully developing the background of the invention and establishing the scope and content of the prior art, the following references are set forth:

(1) L. P. Rodriques, R. Schneerson and J. B. Robbins, Immunity to *Haemophilus influenzae* type b; I The Isolation and Some Physical, Chemical, Serologic and Biologic Properties of the Capsular Polysaccharide of *Haemophilus influenzae* type b. Journal of Immunology, 107, 1071–1079, (1971). This article describes the removal of endotoxins and pyrogenic substances from the polyribosyl ribitol phosphate using chloroform and t-butanol;

(2) P. Anderson and D. H. Smith, Isolation of the Capsular Polysaccharide from the Culture Supernatant of *Haemophilus influenzae* type b. Infection and Immunity, 15, 472–477 (1977). This article describes a method for removing endotoxins and pyrogenic substances from polyribosyl ribitol phosphate using phenol at 4° C. followed by high speed (100,000×g) centrifugation for several hours;

(3) Robbins, J. B., J. C. Parke., R. Schneerson, and J, K. Whisnant, 1973. Quantitative measurement of "Natural" and immunization-induced *Haemophilus influenzae* type b capsular polysaccharide antibodies. Pediatr. Res. 7:103–110;

(4) Smith, D. H., G. Peter, D. L. Ingram, A. L. Harding, and P. Anderson. 1973. Children immunized against *Haemophilus influenzae* type b. Pediatrics 52:637–644;

(5) Anderson, P., D. H. Smith, D. L. Ingram, J. Wilkins, P. F. Wehrle, and V. M. Howie. 1977. Antibody to polyribophosphate of *Haemophilus influenzae* type by in infants and children: Effect of immunization with polyribophosphate. J. Infect. Dis., 136 (Suppl.):557–562. This reference teaches that neither purified PRP alone, or in combination with Diphtheria, pertussis and tetanus provoke humoral activity in young infants against *H. influenzae* type b.

(6) Moxon, E. R., P. Anderson, D. H. Smith, B. Adrianzen, G. G. Graham, and R. S. Baker, 1975. Antibody responses to a combination vaccine against *Haemophilus influenzae* type b, diphtheria, pertussis, and tetanus. Bull. W. H. O. 52:87–90. This reference teaches that the combined vaccine of PRP and diphtheria-pertussis vaccine was less effective than PRP alone; and (7) Limjuco, G. A. and D. J. Carlo. 1976. Endotoxin free Meningococcus polysaccharides. U.S. Pat. No. 3,978,209.

1. Field of the Invention

This invention is in the field of vaccines for immunization against *Haemophilus influenzae type b infections, such as meningitis. More specifically, this invention relateto:* (1) a method for the isolation of antigenic polysaccharide polyribosyl ribitol phosphate (PRP) from *Haemophilus influenzae* type b cultures; and, (2) a process for the preparation of a combined vaccine containing PRP and *B. pertussis* antigens. The PRP of this invention should also be effective when used in conjunction with other non-pathogenic strains of bacteria, such as *E. coli, B. subtilis, S. aureus, B. punilus* and *L. plantarum*, to trigger an antibody response in warm-blooded animals.

2. Description of the Prior Art

The purified polyribitol phosphate (PRP) from *Haemophilus influenzae* type b is being investigated as a protective immunogen, however, an active antigenic response in young animals and infants has not been achieved (see prior art references 1, 3, 4, 5). The prior art method for the purification employed ethanol and Cetavlon (hexadecyltrimethyl ammonium bromide). The contaminants, endotoxins, and pyrogenic substances were removed by the use of cold phenol or chloroform and t-butanol which may result in the loss of the antigenic nature of this polysaccharide (see prior art references 1, 2, 7).

SUMMARY OF THE INVENTION

A new process for the isolation and purification of immunologically active PRP from *Haemophilus influenzae* type b has been established.

The process to be described has distinct advantages over the prior art procedures in that all contaminants (nucleic acids, proteins and endotoxins) are removed to the minimum level by a treatment with hydroxylapatite. The PRP prepared by the process described here gives a higher molecular weight polysaccharide than those reported previously (see prior art references 1, 3, 4).

More importantly, the PRP prepared by this new procedure is highly immunogenic in warm-blooded animals as opposed to the PRP produced by prior art procedures.

A process for removal of contaminants (proteins, nucleis acids and endotoxins) in the polysaccharide PRP is performed formed by treating the partial purified polysaccharide with a phosphate containing adsorbent which does not absorb the polysaccharide under desigated conditions.

The second objective of this invention is to provide a process for the preparation of a combined PRP and pertussis vaccine which is highly immunogenic in young animals.

DISCLOSURE (I) Isolation and purification of polyribosyl ribitol phosphate, the capsular polysaccharide of *Haemophilus influenzae* type b

Organisms, Growth Medium and Culture

Two strains of *Haemophilus influenzae* type b are used. The Rab strain is obtained from Grace Leidy, Babies Hospital, Columbia University, New York City, N.Y. The CK strain was isolated from a patient at Waterbury Hospital Waterbury, Conn. The organisms are passed through mice several times to insure their virulence. The organisms are isolated at autopsy from the brain tissue of mice, subcultured on either 3.7% Brain Heart Infusion (BHI) (Difco Lab., Detroit, Mich.) medium or on 5% BHI agar supplemented with 0.01% nicotinamide adenine dinucleotide (NAD) (P-L Biochemicals, Milwaukee, Wis.) and 1% (v/v) defibrinated horse blood (Animal Blood Center, Syracuse, N.Y.) and then distributed in one ml portions in ampules, lyophilized and stored at −70° C.

Basal medium used for the growth of the organisms is 3.7% (BHI). The basal medium is supplemented with 10 mg of NAD and 20 mg of hemin (Eastman Kodak, Rochester, N.Y.) per liter. One percent (v/v) defibrinated horse blood is added per 50 ml of seed culture. The supplements are freshly prepared and filtered through a 0.45μ Nalgene filter unit Nalge Sybron Corp., Rochester, N.Y.) before use. For growth of the organism in a 14 liter fermentor, the medium is further supplemented with 0.5% glucose.

To prepare a flask of seed organisms, one ml of frozen stock culture is thawed and transferred to 50 ml of the enriched BHI medium supplemented with defibrinated horse blood and NAD. The culture is grown for 8 hours at 37° C. on a gyrotory shaker at 150 rpm. The organisms are added as a 1% inoculum to 500 ml portions of the enriched BHI broth in 2 liter flasks which are then incubated at 37° C. with moderate shaking on a gyrotory shaker for 8 hours (for isolation of PRP) or 14 hours (as seed cultures).

The fermentation of each batch in a 14 liter fermentor is initiated by aseptically transferring 700 ml of the seed culture to 7 liters of the enriched BHI broth supplemented with hemin instead of defibrinated horse blood. The culture is continuously maintained at 37°±1° C. The tank is stirred at a rate of 150 rpm and an air flow of 0.25 liter of air per liter of mash per minute is maintained. During the growth 0.001% of a silicone antifoam (FD-82, Hodag Chemical Corp.) is added as needed. Cultures are grown to the late logarithmic of growth (8 to $10 \times 10^9$ viable cells/ml), usually about 8 hours and then growth is terminated by adding 0.4% formaldehyde and standing overnight at 4° C.

Isolation of Polyribosyl Ribitol Phosphate (PRP)

Culture broth prepared as described above is centrifuged at 27,000×g for 30 minutes at 4° C. The cell free supernatant is collected and treated as follows:

Step 1, Ethanol Precipitation

To the culture supernatant is added sodium acetate (final concentration 4%). The solution is adjusted to pH 6.0–6.2 and 44 liters of 3A ethanol are added slowly with vigorous stirring at 4° C. The mixture is adjusted to pH 6.8 with glacial acetic acid and then allowed to stand for 12 hours at 3° C. The resulting precipitate is collected by decantation and then centrifugation to afford crude PRP.

Step 2, Cetavlon (hexadecyltrimethyl ammonium bromide) Treatment

The precipitate from Step 1 is dissolved in pyrogen-free distilled water and centrifuged to remove the residue. The clear brown solution is then slowly added to 100 ml of a 10% aqueous solution of Cetavlon with mixing (final conc. 0.5%). The mixture is stirred for one hour and then centrifuged. The precipitate of nucleic acids and PRP-Cetavlon complex is mixed with 2 liters of 0.3 M sodium chloride. The cloudy solution is centrifuged to eliminate insoluble materials such as nucleic-Cetavlon salt.

The supernatant is diluted with an equal volume of water causing the PRP-Cetavlon salt to precipitate. The mixture is stirred for one hour, the precipitate is collected by centrifugation and is then dissolved in 2 liters of 0.3 M sodium chloride.

Step 3, Ethanol Precipitation

Cetavlon and the contaminants of nucleic acids and proteins are further removed by ethanol precipitation (at least 2 times). The PRP is precipitated as described in Step 1 while Cetavlon is dissolved in the alcoholic solution. The PRP is recovered by centrifugation, dissolved in 2 liters of pyrogen-free distilled water and then reprecipitated as described above. The final PRP precipitate is solubilized in 20 mM sodium phosphate, pH 6.8.

Step 4, Hydroxylapatite Treatment

Contaminants (e.g. nucleic acids, proteins and endotoxins) in the partial purified PRP preparations are selectively removed by adsorption on a calcium phosphate containing adsorbent such as hydroxylapatite [$3.Ca_3(PO_4)_2 \cdot Ca(OH)_2$].

This invention is based on the discovery that the polysaccharide PRP is not adsorbed by the calcium phosphate adsorbent containing phosphate buffer (20 mM) having a pH of about 6.7–6.9; or a phosphate buffer (50 mM) having a pH of about 5.8; however, the contaminants (such as nucleic acids, proteins and endotoxins) are adsorbed under these conditions. The process of the present invention may be carried out in batch-wise or column operation. In batch process, the hydroxylapatite is added to the partially purified PRP preparation (in 20 mM phosphate; pH 6.9). The mixture is mixed well and centrifuged to remove non-desired solids (adsorbent and the contaminants adsorbed by the adsorbent). The supernatant fluid is subjected to the foregoing procedure at least 2 more times. The resulting solution is filtered through millipore filters, dialyzed against pyrogen-free distilled water, and lyophilized.

In column operation, the partially purified PRP in 20 mM phosphate buffer (pH of at least 5.8) is applied to a column containing the adsorbent hydroxylapatite which had been equilibrated with 20 mM phosphate buffer, pH 5.8 and eluted with a stepwise gradient of sodium phosphate buffer (pH 5.8) from 20 mM to 100 mM. Fractions are collected and assayed for pentose (for polyribosyl ribitol phosphate). Those fractions which are positive for pentose are dialyzed against pyrogen-free distilled water and lyophilized.

(II) A process for preparing a combination vaccine consisting of PRP from *H. influenzae* type b and *B. pertussis* antigens.

To prepare a PRP vaccine, lyophilized PRP (prepared as aforementioned) is dissolved at a concentration of 20 ug/ml in phosphate buffered saline (PBS) (0.113 g potassium diphosphate, 0.83 g disodium phosphate, and 8.5 g sodium chloride per liter, pH 7.0, containing 0.01% thimerosal). The vaccine is sterile filtered through 0.45μ millipore filter units, dispensed into glass vials, and stored at 4° C.

A concentrated solution of the PRP is prepared by weighing predetermined amounts of the polysaccharide and dissolving it in phosphate buffered saline (0.113 g potassium diphosphate, 0.83 g disodium phosphate, and 8.5 g sodium chloride per liter, pH 7.0, containing 0.01% thimerosal). This concentrated solution of PRP is then mixed with an appropriate volume of fresh *B. pertussis* cell suspensions to prepare the stock solution. The combined vaccine in this stock solution contains 200 μg of PRP and approximately 70 oapacity units (op) of cells per ml. The stock solution is kept at 4° C. for 90 days to allow for detoxification of pertussis antigens before the final product (vaccine) is prepared (which contains 10 μg of PRP and 3.5 op units of pertussis cells/0.5 ml dose).

filtration on columns 1.5×90 cm (Pharmacia-Fine Chemicals, Piscataway, N.J.). Partition coefficient (Kd) values are calculated from the elution pattern developed by the orcinal reaction (Herbert, et al., Methods in Microbiology, Vol. 5B, 285-291.

Table I

| | Physical-Chemical Characteristics of PRP Preferred | | | | | |
|---|---|---|---|---|---|---|
| | Assay | | | | Endotoxin | |
| Procedure | Mol. Size (Kd) | Pentose (%) | Nucleic Acid (%) | Protein (%) | Rabbit Pyrogen Test[c] | Limulus Lysate Test[d] |
| Example 1 | 0[a] | 36.0 | 0.8 | 0.7 | 10.0 | 1/400 |
| Example 2 | 0.44[b] | 33.8 | 0.3 | 0.7 | 10.0 | 1/1000 |

[a]Using both Sepharose 2B and 4B, molecular weight >2KID[7]
[b]Using Sepharose 4B
[c]μg PRP/kg rabbit body weight not yielding fever
[d]Reciprocal dilution of PRP (100 μg PRP/ml) when compared to Bureau of Biologics E1 (endotoxin standard)

DETAILED DISCLOSURE

EXAMPLE 1

Hydroxylapatite (e.g. Bio. gel HTP, Bio-Rad Laboratories, Richmond, Calif.), 2.5 g is added to 250 ml partially purified PRP preparations (after Cetavlon and ethanol treatments) (containing approximately 1.0 mg PRP/ml) in 20 mM sodium phosphate buffer, pH 6.9 and mixed at ice-cold water bath (1°-4° C.) for one hour. The mixture is centrifuged in the Sorvall RC2-B for 30 minutes at 16,000×g. The supernatant fluid is then passed through 0.65μ millipore filter and subjected to the foregoing procedure (each time treated with 2.5 g hydroxylapatite) 2 more times. The resulting solution is filtered through 0.65μ and 0.45μ millipore filters, dialyzed against pyrogen-free distilled water and lyophilized. The lyophilized product exhibits strong immunogenic activity (see below combined vaccine and animal experiment) and contains very low contaminants (such as nucleic acids, proteins and endotoxins) (see Table I below). Approximately 170 mg of the lyophilized PRP is obtained. The recovery of PRP by this process is approximately 70% of the starting polysaccharide. The PRP should be stored under suitable conditions, such as at 4° C. in a desiccator over phosphorus pentoxide and silica gel.

EXAMPLE 2

A partially purified PRP (300 mg PRP) is dissolved in 100 ml of 20 mM sodium phosphate buffer, pH 5.8 (i.e. 3 mg PRP/ml). This solution is applied to a column at ambient temperature (5.0×45 cm) of hydroxylapatite (approximately 250 ml bed volume which has been equilibrated with 20 mM sodium phosphate buffer, pH 5.8 and eluted with a stepwise gradient of 20 mM, 50 mM, 100 mM sodium phosphate buffer, pH 5.8. The individual fractions (200 ml) eluted with 20 mM and 50 mM sodium phosphate buffer (pH 5.8), positive for pentose (pentose determination by the orcinal method) are collected, dialyzed against pyrogen-free distilled water and lyophilized. Approximately 206 mg of the lyophilized product, PRP, is obtained.

The purity of the polysaccharide, PRP is assayed by estimating to what extent they are contaiminated with nucleic acids, proteins and endotoxins. Protein concentration is determined by the method of Lowry, et al. in J. Biol. Chem. 193:265 (1951) with boving serum albumin as standard. Nucleic acid is measured by the absorption of the PRP solution at 260 nm. The absorbance of 50 μg of nucleic acid in one ml of water in a cell of 1-cm light path is assumed to be equal to 1.0. Molecular size is estimated by means of Sepharose 4B or 2B gel

EXAMPLE 3

A combination vaccine containing PRP from $H.$ $influenzae$ type b and $B.$ $pertussis$ antigens is prepared as follows: 140 mg PRP (as prepared in Example 2) is dissolved in 350 ml sterile phosphate buffered saline (PBS) (0.113 g potassium diphosphate, 0.83 g disodium phosphate, and 8.5 g sodium chloride per liter, pH 7.0, containing 0.01% thimerosal), and filter through 0.45μ millipore filter. This concentrated PRP solution (400 μg/ml) is used to prepare a combination vaccine which consists of PRP and $B.$ $pertussis$ antigens.

To 150 ml of the concentrated PRP solution (400 μg/ml) add 150 ml of fresh $B.$ $pertussis$ (strain 138) cell suspension in PBS, pH 7.0 (containing 149 opacity; op, unit cells/ml) to prepare the stock solution of the combined vaccine. This stock solution (300 ml) is kept at 4° C. until the endotoxin level of the pertussis is decreased (at least 90 days). The sterility of the stock solution is tested with thioglycollate media (at 32°-33° C.). The pH of the stock solution after 90 days incubation is checked and adjusted to pH 7.0±1. The final product (vaccine) used for animal experiments is prepared by diluting the stock combined solution with PBS and it contains 10 μg of PRP and 3.5 op units of pertussis cells/0.5 ml (dose).

The results of the antibody response to this combined vaccine in young rats appears in FIGS. 1 and 2 as shown below.

EXAMPLE 4

The stock solution of PRP (400 μg/ml) is prepared by dissolving 30 mg PRP (as prepared in Example 1) in 75 ml sterile phosphate buffered saline (PBS) and filtered through 0.45μ millipore filter. To 25 ml of this concentrated PRP is added an equal volume (i.e. 25 ml) of fresh $B.$ $pertussis$ (strain 138) cell suspension in PBS, pH 7.0 (containing 149 op units cells/ml) to prepare the stock solution of the combined vaccine. This stock solution (50 ml) is kept at 4° C. for (at least) 90 days. The sterility of the stock solution is tested as aforementioned with thioglycollate media. The pH of the stock solution is pH 7.0±1. The final product (vaccine) used for animal experiments is prepared by diluting the stock combined solution with PBS, and it contains 10 μg of PRP and 3.7 op units of pertussis cells/0.5 ml (dose).

EXAMPLE 5

The PRP stock solution (200 μg/ml in PBS (pH 7.0) is prepared as in Example 4. The pertussis stock solution (containing 75 op units/ml) is prepared by diluting 25 ml of fresh $B.$ $pertussis$ cell suspension (149 op units/ml)

with an equal volume of PBS. Both stock solutions are incubated separately at 4° C. for 90 days or slightly longer. The combined vaccine is made by taking 14 ml of PRP stock solution (200 μg/ml), plus 14 ml (detoxified) stock solution of pertussis antigens (75 op units/ml) and diluting it with 112 ml PBS (final val. 140 ml). The final vaccine used for animal experiments contains 10 μg PRP and 3.7 op units pertussis/0.5 ml (dose).

The results of the antibody response to this combined vaccine in young rats appears in FIG. 3 and in Table II.

TABLE II

Immunogenicity of PRP-Pertussis Complex in Young Rats[a]

| Vaccine | Dose (single or multiple) | Anti-PRP Antibody Activity (cpm $^3$H-PRP Bound/50 μl Serum) | | | | 3rd Week Post-injection (fold increase from preimmunization) |
|---|---|---|---|---|---|---|
| | | Week Post-Injection | | | | |
| | | 0 | 1 | 2 | 3 | |
| Phosphate Buffered Saline | (M)[b] | 99[c] | 116 | 107 | 158 | 1.6 |
| Pertussis | (M) | 113 | 108 | 117 | 149 | 1.3 |
| PRP (K) (Example 1) | (M) | 110 | 136 | 148 | 142 | 1.3 |
| PRP (K) (3 mo) | (S)[d] | 108 | 136 | 132 | 147 | 1.4 |
| + Pertussis (3 mo) (Example 5) | (M) | 101 | 135 | 1002 | 1771 | 17.5 |
| PRP (K)+Pertussis (3 mo) (Example 4) | (S) | 93 | 146 | 135 | 140 | 1.5 |
| | (M) | 119 | 154 | 751 | 1410 | 11.8 |

[a]10 μg PRP or 3.5 op units pertussis/dose (0.5 ml).
[b]Booster - 2nd and 3rd week respectively (multiple injection).
[c]Average 10 rats.
[d]Single injection.

I claim:

1. In a method of isolating and purifying immunologically active polyribosyl ribitol phosphate (PRP), the capsular polysaccharide of *Haemophilus influenzae* type b, fermenting strains of the organism *Haemophilus influenzae* type b under conditions suitable for the production of said polysaccharide, further isolating the PRP as a hexadecyltrimethyl ammonium bromide complex, the improvement comprising:

purifying the PRP by adding hydroxylapatite [3.Ca$_3$(PO$_4$)$_2$Ca(OH)$_2$] in a 0.02 M sodium phosphate buffer at a pH from about 6.7 to about 6.9, mixing at a temperature of about 4° C., centrifuging, removing the supernatant and repeating the foregoing procedure at least two more times, filtering the supernatant through suitable filters, dialyzing against pyrogen-free distilled water, and then lyophilizing.

2. In a method of isolating and purifying, the capsular polysaccharide of *Haemophilus influenzae* type b, fermenting strains of the organism *Haemophilus influenzae* Type b under conditions suitable for the production of said polysaccharide, further isolating the PRP as a hexadecyltrimethyl ammonium bromide complex, the improvement comprising:

purifying the PRP by column chromatography in a 0.02 M sodium phosphate buffer at a pH of about 5.8 through hydroxylapatite [3Ca$_3$(PO$_4$)$_2$.Ca(OH)$_2$], eluting with a stepwise gradient of 0.02 M and 0.05 M sodium phosphate buffer at a pH of about 5.8, isolating fractions by analysis for PRP, dialyzing said fractions against pyrogen-free distilled water and then lyophilizing.

* * * * *